United States Patent [19]

Miura et al.

[11] Patent Number: 4,785,132
[45] Date of Patent: Nov. 15, 1988

[54] PROCESS FOR PREPARING CYCLOHEXANONECARBOXYLIC ACID COMPOUNDS

[75] Inventors: Tohru Miura; Teruyuki Nagata; Hideki Mizuta, all of Ohmuta, Japan

[73] Assignee: Mitsui Toatsu Chemicals, Incorporated, Tokyo, Japan

[21] Appl. No.: 29,881

[22] Filed: Mar. 25, 1987

[30] Foreign Application Priority Data

Aug. 21, 1986 [JP] Japan .................................. 61-193986

[51] Int. Cl.$^4$ ............................................ C07C 67/303
[52] U.S. Cl. ...................................... 560/126; 562/508
[58] Field of Search ........................ 560/126; 562/508; 568/362

[56] References Cited

U.S. PATENT DOCUMENTS

| | | | |
|---|---|---|---|
| 2,873,296 | 2/1958 | Nilsson et al. | 568/362 |
| 4,326,997 | 4/1982 | Willis et al. | 568/362 X |
| 4,409,401 | 10/1983 | Murtha | 568/362 |
| 4,537,704 | 8/1985 | Sprecker et al. | 252/522 R |

OTHER PUBLICATIONS

J. Am. Chem., 86, 15, (1962), pp. 3068 to 3072.

*Primary Examiner*—Michael L. Shippen
*Attorney, Agent, or Firm*—Fisher, Christen & Sabol

[57] ABSTRACT

A process for preparing cyclohexanonecarboxylic acid compounds by catalytically hydrogenating the corresponding hydroxybenzoic acid compounds in a secondary alcohol or tertiary alcohol solvent.

10 Claims, No Drawings

PROCESS FOR PREPARING CYCLOHEXANONECARBOXYLIC ACID COMPOUNDS

BACKGROUND OF THE INVENTION a. Field of the Invention

This invention relates to a process for preparing cyclohexanonecarboxylic acid compounds.

b. Description of the Prior Art

Cyclohexanonecarboxylic acid compounds, such as cyclohexanone-4-carboxylic acid and the like, are known to be useful as perfume enhancers and the like (see U.S. Pat. No. 4,537,704). Moreover, these compounds are also useful as starting materials for the synthesis of polymers and as intermediates for the synthesis of liquid crystals. A large number of processes for the synthesis of cyclohexanonecarboxylic acid compounds have been proposed. Among them, the process which comprises hydrogenating a hydroxybenzoic acid compound and selectively oxidizing the resulting cyclohexanolcarboxylic acid compound with the aid of an oxidizing agent such as a chromium compound or the like [as described in J. Am. Chem. Soc., 86(15), 3068-72 (1962)] is considered to be useful for inductrial purposes.

On the other hand, an attempt has been made to prepare cyclohexanone-4-carboxylic acid methyl or ethyl ester by direct and selective hydrogenation of methyl or ethyl p-hydroxybenzoate (see U.S. Pat. No. 4,537,704).

Of these two processess, the former one in which a cyclohexanonecarboxylic acid compound is prepared by way of a cyclohexanolcarboxylic acid compound involves two process steps. Moreover, the hydrogenation step yields such by-products as the dehydroxylated product, lactonized product and the like, and the oxidation step fails to give a satisfactory yield. Furthermore, it is necessary to recover and regenerate the oxidizing agent. Thus, it is hard to say that this process is highly economical.

On the other hand, the process of U.S. Pat. No. 4,537,704 based on the direct hydrogenation of methyl or ethyl p-hydroxybenzoate is hardly applicable to high-melting compounds such as p-hydroxybenzoic acid, because the reaction is carried out in the absence of solvent. Moreover, where methyl p-hydroxybenzoate, for example, is hydrogenated, the over-hydrogenated product (i.e., cyclohexanol-4-carboxylic acid methyl ester) is formed as a by-product in an amount of 30% or more. Thus, the yield of cyclohexanone-4-carboxylic acid methyl ester is less than satisfactory.

SUMMARY OF THE INVENTION

It is an object of the present invention to provide a process for preparing cyclohexanonecarboxylic acid compounds by catalytic hydrogenation of hydroxybenzoic acid compounds which makes it possible to inhibit the formation of by-products and thereby produce the desired compound in high yield and with good economy.

As a result of investigation on the direct hydrogenation of hydroxybenzoic acid compounds, the present inventors have found that, although the reaction never proceeds in some solvents, the use of a secondary alcohol or tertiary alcohol as the solvent enhances the reaction rate and selectivity and thereby permits the direct hydrogenation of hydroxybenzoic acid compounds while minimizing the formation of cyclohexanol-4-carboxylic acid compounds.

According to the present invention, there is provided a process for preparing cyclohexanonecarboxylic acid compounds of the formula

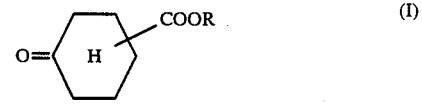

where R is a hydrogen atom or an alkyl group having 1 to 3 carbon atoms, which comprises catalytically hydrogenating a hydroxybenzoic acid compound of the formula

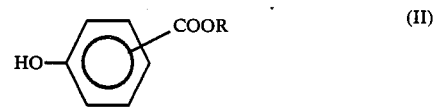

where R is as defined for formula (I), in a secondary alcohol or tertiary alcohol solvent.

DETAILED DESCRIPTION OF THE INVENTION

As described above, when a hydroxybenzoic acid compound of formula (II) is catalytically hydrogenated to obtain the corresponding cyclohexanonecarboxylic acid compound of formula (I), a cyclohexanolcarboxylic acid compound of the formula

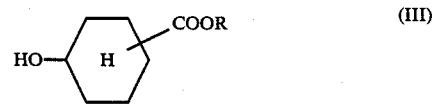

where R is as defined for formula (I), is formed as a by-product in large amounts. Upon exposure to heat, this compound of formula (III) is converted into its lactone derivative with elimination of water or an alcohol.

For example, cyclohexanol-4-carboxylic acid methyl ester is easily converted into 2-oxabicyclo-[2,2,2]octan-3-one with elimination of methanol. Since this lactone derivative has a boiling point slightly different from that of cyclohexanone-4-carboxylic acid methyl ester, their separation by distillation requires a very large number of theoretical plates and a very high reflux ratio. Moreover, a considerable loss of cyclohexanone-4-carboxylic acid methyl ester is caused during the separation. Thus, when the reaction mass is distilled to isolate the cyclohexanonecarboxylic acid compound of formula (I), the compound of formula (III) tends to undergo lactonization during the distillation. The resulting lactone derivative is hard to separate from the cyclohexanonecarboxylic acid compound of formula (I) and, moreover, causes a considerable loss of the compound of formula (I) during the separation.

More specifically, in order to obtain the desired product of the present invention, i.e. the desired cyclohexanonecarboxylic acid compound of formula (I), in highly purified form and in high yield, it is necessary not only to enhance the reaction rate, but also to minimize the formation of the cyclohexanolcarboxylic acid compound of formula (III). To this end, it has been found that the reaction should be carried out in a secondary alcohol or tertiary alcohol solvent.

The secondary alcohol or tertiary alcohol solvent used in the reaction of the present invention is selected from among such compounds as are liquids at the reaction temperature employed and do not undergo hydrogenation under the reaction conditions employed. Usable solvents include, for example, aliphatic secondary alcohols such as isopropyl alcohol, sec-butyl alcohol, sec-amyl alcohol, diethylcarbinol, methylisobutylcarbinol, 3-heptanol, methylamylcarbinol, etc., alicyclic secondary alcohols such as cyclopentanol, cyclohexanol, cyclooctanol, 2-methylcyclohexanol, 3-methylcyclohexanol, 4-methylcyclohexanol, dimethylcyclohexanol, trimethylcyclohexanol, etc.; aromatic secondary alcohols such as methylphenylcarbinol, etc.; and tertiary alcohols such as tert-butyl alcohol, tert-amyl alcohol, 1-methylcyclohexanol, etc.

Among these solvents, isopropyl alcohol is most preferred in consideration of its effectiveness in inhibiting the formation of compounds of formula (III), its ease of separation and recovery after completion of the reaction, and its low price.

The solvent is usually used in an amount of 0.5 to 5 parts by weight, preferably 1 to 3 parts by weight, for each part by weight of the hydroxybenzoic acid compound of formula (II).

The over-hydrogenated products of formula (III) formed as by-products in the reaction of the present invention, such as cyclohexanol-2-carboxylic acid methyl ester, cyclohexanol-2-carboxylic acid ethyl ester, cyclohexanol-3-carboxylic acid methyl ester, cyclohexanol-3-carboxylic acid ethyl ester, cyclohexanol-4-carboxylic acid methyl ester, cyclohexanol-4-carboxylic acid ethyl ester and the like, are also secondary alcohols having an inhibitory effect on the formation of compounds of formula (III). However, they cannot be used in the practice of the present invention because, as described above, their use makes it difficult to isolate the desired cyclohexanonecarboxylic acid compound during the purification procedure.

The compounds of formula (II) which can be used in the practice of the present invention include hydroxybenzoic acids, hydroxybenzoic acid methyl esters, hydroxybenzoic acid ethyl esters, and hydroxybenzoic acid propyl esters. By using them in the process of the present invention, the corresponding ketone compounds of formula (I) can be obtained in high yields.

The process of the present invention is especially preferable for the preparation of cyclohexanone-4-carboxylic acid methyl ester from methyl p-hydroxybenzoate and can give satisfactorily high yields.

The reaction of the present invention is usually carried out in the presence of a catalyst. Although any of conventional hydrogenation catalysts may be used for this purpose, platinum metal-containing catalysts and rhenium-containing catalysts are preferred. Among others, palladium-carbon catalyst is most preferred.

The catalyst is usually used in an amount of 0.0001 to 0.2 gram atom, preferably 0.0003 to 0.01 gram atom, of catalyst metal atoms for each mole of the hydroxybenzoic acid compound of formula (II).

The reaction of the present invention is usually carried out at a reaction temperature of 80° to 200° C. and a hydrogen pressure of 1 to 50 kg/cm², preferably 2 to 30 kg/cm². It is not advisable to employ hydrogen pressures higher than 50 kg/cm², because this cause an increased formation of by-products.

The cyclohexanonecarboxylic acid compound formed by the reaction of the present invention can be isolated by distilling off the solvent and then purifying the residue according to conventional procedures such as distillation, recrylstallization and the like.

The process of the present invention is more specifically explained with reference to the following examples.

EXAMPLES 1-3

Into a stainless steel autoclave were charged 45.6 g (0.30 mole) of methyl p-hydroxybenzoate, 0.23 g of 5% palladium-carbon catalyst, and 100 ml of each of the secondary or tertiary alcohols shown in Table 1 below. After the air within the autoclave was displaced with nitrogen gas, the reaction mixture was allowed to absorb 0.60 mole of hydrogen at a temperature of 180° C. and a gauge pressure of 20 kg/cm². After the reaction mixture was cooled and filtered to remove the catalyst therefrom, the cyclohexanol-4-carboxylic acid methyl ester and cyclohexanol-4-carboxylic acid methyl ester contents of the resulting reaction mass were determined by gas chromatography. The results thus obtained are shown in Table 1 below.

TABLE 1

| Example | Solvent | Reaction time (minutes) | Yield (%) of desired product* | Content (%) of over-hydrogenated product** |
|---------|---------|-------------------------|-------------------------------|---------------------------------------------|
| 1 | Isopropyl alcohol | 170 | 77.6 | 15.0 |
| 2 | Cyclohexanol | 360 | 72.8 | 18.1 |
| 3 | tert-Butyl alcohol | 270 | 61.9 | 25.4 |

*Cyclohexanone-4-carboxylic acid methyl ester.
**Cyclohexanol-4-carboxylic acid methyl ester.

Next, the reaction mass obtained in Example 1 was evaporated to separate the isopropyl alcohol therefrom. Then, using a distillation column packed with Dickson's packing material and having a number of theoretical plates of 20, the residue was distilled at a reflux ratio of 2-10 to obtain 33.2 g of cyclohexanone-4-carboxylic acid methyl ester as the distillate at 144° C./30 mmHg. This product had a purity of 96%, and the greater part of the impurities comprised 2-oxabicyclo-[2,2,2]octan-3-one

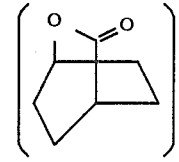

EXAMPLE 4

Into a stainless steel autoclave were charged 41.4 g (0.30 mole) of p-hydroxybenzoic acid, 2.1 g of 5% palladium-carbon catalyst, and 100 ml of 2-propyl alcohol. After the air within the autoclave was displaced with nitrogen gas, the reaction mixture was allowed to absorb 0.60 mole of hydrogen at a temperature of 120° C. and a gauge pressure of 20 kg/cm². After the reaction mixture was cooled and filtered to remove the catalyst therefrom, the solvent was distilled off to obtain 42.8 g of white crystals. Gas chromatographic analysis revealed that this product had a cyclohexanone-4-carboxylic acid content of 40.2% and its yield was 40.3%.

COMPARATIVE EXAMPLES 1-6

Hydrogenation was carried out in the same manner as described in Examples 1-3, except that there were used each of the reaction times shown in Table 2 below and 100 ml of each of the solvents (other than the secondary alcohol and tertiary alcohol solvents within the scope of the present invention) shown in Table 2 below. The resulting reaction mixtures were worked up and analyzed in the same manner as described in Examples 1-3. The results thus obtained are shown in Table 2. In all cases, the reaction rate was so low that the reaction was discontinued before completion.

TABLE 2

| Comparative Example | Solvent | $H_2$ absorption (% equivalent) | Reaction time (minutes) | Yield (%) |
| --- | --- | --- | --- | --- |
| 1 | Methanol | 5 (discontinued) | 60 | 3.5 |
| 2 | Ethanol | 10 (discontinued) | 60 | 7.8 |
| 3 | Acetic acid | — (no absorption) |  | 0 |
| 4 | Water | 20 (discontinued) | 80 | 13.5 |
| 5 | Toluene | 65 (discontinued) | 360 | 49.0 |
| 6 | None | 50 (discontinued) | 360 | 31.9 |

COMPARATIVE EXAMPLE 7

Reaction was carried out in the same manner as described in Example 1, except that 100 ml of cyclohexanol-4-carboxylic acid methyl ester formed as a by-product during the hydrogenation of methyl p-hydroxybenzoate was used as the solvent. After the reaction mixture was filtered to remove the catalyst therefrom, the resulting reaction mass was analyzed by gas chromatography. The yield of cyclohexanone-4-carboxylic acid methyl ester was 82.0%.

Then, the reaction mass thus obtained was distilled in the same manner as described in Example 1 to obtain 44.7 g of distillate at 144° C./30 mmHg. This product had a purity of 61%, and the greater part of the impurities comprised 2-oxabicyclo[2,2,2]octan-3-one.

EXAMPLE 5

Hydrogenation was carried out in the same manner as described in Example 1, except that the methyl p-hydroxybenzoate was replaced by methyl salicylate. The resulting reaction mixture was worked up in the same manner as described in Example 1 to obtain cyclohexanone-2-carboxylic acid methyl ester having a boiling point of 105° C./20 mmHg. Its yield was 42%.

EXAMPLE 6

Hydrogenation was carried out in the same manner as described in Example 1, except that the methyl p-hydroxybenzoate was replaced by ethyl m-hydroxybenzoate. The resulting reaction mixture was worked up in the same manner as described in Example 1 to obtain cyclohexanone-3-carboxylic acid ethyl ester having a boiling point of 131° C./10 mmHg. Its yield was 13%.

What is claimed is:
1. A process for preparing cyclohexanonecarboxylic acid compounds of the formula:

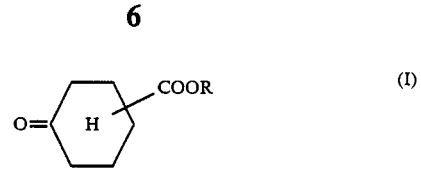

wherein R is a hydrogen atom or an alkyl group having 1 to 3 carbon atoms, which comprises catalytically hydrogenating a hydroxybenzoic acid compound of the formula:

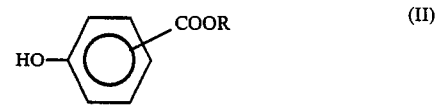

wherein R is as defined in formula (I), in a tertiary alcohol solvent or a secondary alcohol solvent other than a cyclohexanolcarboxylic acid compound of the formula:

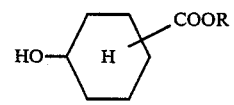

wherein R is as defined in formula (I).
2. A process as claimed in claim 1 wherein the cyclohexanonecarboxylic acid compound is cyclohexanone-4-carboxylic acid methyl ester and the hydroxybenzoic acid compound is methyl p-hydroxybenzoate.
3. A process as claimed in claim 1 wherein the secondary alcohol solvent is an aliphatic, alicyclic or aromatic secondary alcohol.
4. A process as claimed in claim 1 wherein the tertiary alcohol solvent is an aliphatic or alicyclic tertiary alcohol.
5. A process as claimed in claim 1 wherein the secondary alcohol solvent is isopropyl alcohol.
6. A process as claimed in claim 1 wherein the secondary alcohol or tertiary alcohol solvent is used in an amount of 0.5 to 5 parts by weight for each part by weight of the hydroxybenozic acid compound of formula (II).
7. A process as claimed in claim 1 wherein the catalyst is a platinum metal-containing catalyst or a rhenium-containing catalyst.
8. A process as claimed in claim 1 wherein the catalyst is a palladium-carbon catalyst.
9. A process as claimed in claim 1 wherein the hydrogenation is carried out at a reaction temperature of 80° to 200° C. and a hydrogen pressure of 1 to 50 kg/cm$^2$.
10. A process as claimed in claim 1 wherein the secondary alcohol is selected from the group consisting of isopropyl alcohol, sec-butyl alcohol, sec-amyl alcohol, diethylcarbinol, methylisobutylcarbinol, 3-heptanol, methylamylcarbinol, cyclopentanol, cyclohexanol, cyclooctanol, 2-methylcyclohexanol, 3-methylcyclohexanol, 4-methylcyclohexanol, dimethylcyclohexaol, trimethylcyclohexanol, methylphenylcarbinol, tert-butyl alcohol, tert-amyl alcohol and 1-methylcyclohexanol.

* * * * *